US00PP11341P

United States Patent [19]

Olbring

[11] Patent Number: Plant 11,341

[45] Date of Patent: Apr. 11, 2000

[54] POINSETTIA PLANT NAMED 'ECKADALI'

[75] Inventor: Andreas Olbring, Nipomo, Calif.

[73] Assignee: Paul Ecke Ranch, Inc., Encinitas, Calif.

[21] Appl. No.: 09/087,916

[22] Filed: Jun. 1, 1998

[51] Int. Cl.[7] ..... A01H 5/00

[52] U.S. Cl. ..... Plt./304

[58] Field of Search ..... Plt./304, 305

[56] References Cited

U.S. PATENT DOCUMENTS

P.P. 9,739 12/1996 Dummen ..... Plt./304

P.P. 10,824 3/1999 Zerr ..... Plt./304

OTHER PUBLICATIONS

GTITM UPOVROM Citation for 'Ecke 66–97' as Per CA PBR 98–1315; Mar. 31, 1998.

Plant Varieties Journal, No. 32, pp. 57 and 58; Jul. 1999.

*Primary Examiner*—Howard J. Locker

*Assistant Examiner*—Kent L. Bell

*Attorney, Agent, or Firm*—C. A. Whealy

[57] ABSTRACT

A new and distinct variety of Poinsettia plant named 'Eckadali', characterized by its creamy white flower bracts; extremely dark green leaves; compact plant habit, freely branching habit; and excellent postproduction longevity.

1 Drawing Sheet

BACKGROUND OF THE INVENTION

The present invention relates to a new and disticnt variety of Poinsettia plant, botanically known as *Euphorbia pulcherrima* Willd., and hereinafter referred to by the name 'Eckadali'.

The new variety is a spontaneous branch mutation of the commercial *Euphorbia pulcherrima* Willd. cultivar 'Red Splendor', disclosed in U.S. Plant Pat. No. 9,632. The new Poinsettia was selected by the Inventor in a greenhouse in Nipomo, Calif., in 1997. The objective of the Inventor's Poinsettia development program is to create new Poinsettia cultivars having desirable bract and foliage color and form, strong and freely branching stems and good post-production longevity.

Asexual reproduction of the new variety by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadali'. These characteristics in combination distinguish 'Eckadali' as a new and distinct variety:

1. Creamy white flower bracts.
2. Extremely dark green leaves.
3. Compact plant habit.
4. Very freely branching habit.
5. Excellent postproduction longevity.

In side-by-side comparisons conducted by the Inventor in Encinitas, Calif., plants of the new Poinsettia differed from plants of 'Red Splendor' in the following characteristics:

1. Plants of the new Poinsettia have white-colored flower bracts whereas plants of the cultivar 'Red Splendor' have red-colored flower bracts.

2. Plants of the new Poinsettia are more compact than plants of the cultivar 'Red Splendor'.

3. Inflorescences of plants of the new Poinsettia are smaller than inflorescences of plants of 'Red Splendor'.

BRIEF DESCRIPTION OF THE PHOTOGRAPH

The accompanying colored photograph illustrates the overall appearance of the new variety, showing the colors as true as it is reasonably possible to obtain in a colored reproduction of this type. The photograph comprises a side perspective view of a typical plant of 'Eckadali'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 22 to 24° C., night temperatures about 16 to 18° C. and light levels about 40,000 lux. Plants were grown in 16.5—cm pots, pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Eckadali'.

Parentage: Spontaneous branch mutation of *Euphorbia pulcherrima* Willd. cultivar 'Red Splendor', disclosed in U.S. Plant Pat. No. 9,632.

Propagation:

*Type cutting.*—Terminal cuttings.

*Time to initiate roots.*—Summer: About 12 to 18 days at 27° C. Winter: About 15 to 18 days at 24° C.

*Time to develop roots.*—Summer: About 26 days at 27° C. Winter: About 26 days at 24° C.

*Rooting habit.*—Thick, freely branching, becoming more fibrous with subsequent development.

Plant description:

*Plant form.*—Inverted triangle, rounded plant canopy.

*Growth habit.*—Compact, upright and slightly spreading. Very freely branching, branching is enhanced by removing the shoot apex. Moderate growth rate and moderately vigorous.

*Plant height.*—About 27 cm.

*Crop time.*—From unrooted cuttings to a flowering plant in a 16.5—cm container, about 19 weeks are required.

*Stem description.*—Number of lateral branches: About ten lateral branches are formed after removal of the terminal apex. Lateral branch length: About 20.5 cm. Internode length: About 1.25 cm. Stem color: 146A.

*Foliage description.*—Quantity of leaves per lateral branch: About 15. Length: About 8.5 cm. Width: About 6 cm. Shape: Ovate. Apex: Broadly acuminate. Base: Acute. Margin: Entire. Texture: Velvety, dull, mostly glabrous with very slight pubescence on lower surface. Aspect: Mostly flat. Color: Young foliage, upper surface: Darker than 147A. Young foliage, lower surface: 137B. Mature foliage, upper surface: Much darker than 147A, almost black, but greener than 202A. Mature foliage, lower surface: 147A. Venation, upper surface: 147B. Venation, lower surface: 147C. Petiole: Length: About 3.5 cm. Diameter: About 2 mm. Color: 146C.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Quantity of inflorescences.*—One per lateral branch, usually about ten per plant.

*Inflorescence size.*—Diameter: About 21 cm. Height (depth): About 3 cm.

*Flower bracts.*—Quantity of flower bracts per inflorescence: Usually about 7 primary bracts and about 9 secondary bracts per inflorescence. Length: About 12 cm. Width: About 9 cm. Shape: Ovate, older bracts slightly lobed. Apex: Abruptly acuminate. Base: Acute. Margin: Mostly entire, older bracts slightly lobed. Texture: Smooth, slightly glabrous. Aspect: Flat. Color: Developing, upper surface: 10C. Developing, lower surface: 8C. Mature, upper surface: 10C/10D. Mature, lower surface: 8C.

*Cyathia.*—Quantity: Usually about 21 per corymb. Diameter of cyathia cluster: About 3.5 cm. Length: About 1.2 cm. Width: About 5 mm. Color: Immature: 144A. Mature: 144B at base with 14A ring at apex of nectary. Peduncle: Length: About 2 mm. Aspect: Strong, erect. Color: 144B. Stamens: Stamen number: Typically two to five per cyathium. Anther size: About 1 mm. Anther shape: Oval. Anther color: 8A. Amount of pollen: Low. Pollen color: 8A. Pistils: Pistil number: 1 per cyathium. Stigma shape: Five-parted. Stigma color: 8A. Style length: About 2 mm. Style color: 144C. Nectary color: 14A.

Disease resistance: No fungal, bacterial nor viral problems observed on plants grown under commercial conditions.

Postproduction longevity: Generally plants maintain good substance and bract color for about four weeks under interior conditions.

It is claimed:

1. A new and distinct variety of Poinsettia plant named 'Eckadali', as illustrated and described.

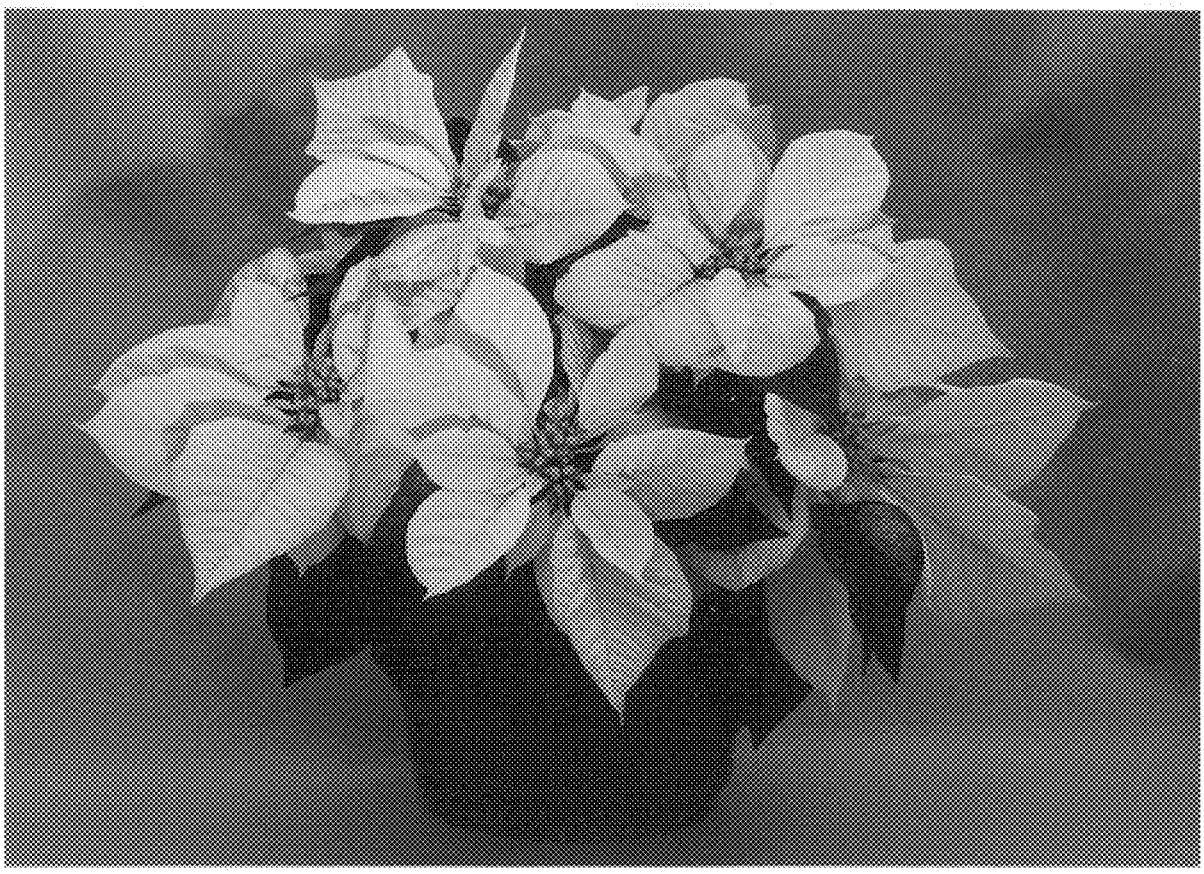

* * * * *